(12) United States Patent
Sakurai

(10) Patent No.: US 11,981,836 B2
(45) Date of Patent: May 14, 2024

(54) SILICONE PRESSURE-SENSITIVE ADHESIVE AND SILICONE PRESSURE-SENSITIVE ADHESIVE COMPOSITION

(71) Applicant: 3M INNOVATIVE PROPERTIES COMPANY, St. Paul, MN (US)

(72) Inventor: Aizoh Sakurai, Tokyo (JP)

(73) Assignee: 3M Innovative Properties Company, Saint Paul, MN (US)

(*) Notice: Subject to any disclaimer, the term of this patent is extended or adjusted under 35 U.S.C. 154(b) by 361 days.

(21) Appl. No.: 17/292,646

(22) PCT Filed: Nov. 8, 2019

(86) PCT No.: PCT/IB2019/059631
§ 371 (c)(1),
(2) Date: May 10, 2021

(87) PCT Pub. No.: WO2020/099999
PCT Pub. Date: May 22, 2020

(65) Prior Publication Data
US 2022/0002601 A1  Jan. 6, 2022

(30) Foreign Application Priority Data
Nov. 15, 2018 (JP) ................. 2018-214906

(51) Int. Cl.
*B32B 41/00* (2006.01)
*A61L 24/04* (2006.01)
(Continued)

(52) U.S. Cl.
CPC .......... *C09J 183/04* (2013.01); *A61L 24/046* (2013.01); *C08G 77/08* (2013.01); *C08G 77/12* (2013.01);
(Continued)

(58) Field of Classification Search
CPC ...... C09J 183/04; C09J 7/38; C09J 2301/122; C09J 2301/302; A61L 24/046;
(Continued)

(56) References Cited

U.S. PATENT DOCUMENTS 4,831,070 A   5/1989  McInally
5,162,410 A   11/1992  Sweet
(Continued)

FOREIGN PATENT DOCUMENTS

JP   1995-H07-258624   10/1995
JP   2016-501942       1/2017
(Continued)

OTHER PUBLICATIONS

"Liveo™ BIO-PSA 7-4560", Silicone Adhesives, DuPont, Product Information of Dow Corning Bio-PSA 7-4560, [retrieved from the internet on Sep. 3, 2020], URL <http://www.healthcare-plus.com.tw/big5/pdf/02-06.pdf#search=%27bio+PSA+74560%27>, 2020, pp. 1-2.
(Continued)

*Primary Examiner* — Michael N Orlando
*Assistant Examiner* — Joshel Rivera

(57) ABSTRACT

Silicone pressure-sensitive adhesives is the reaction product of a composition including a silanol end group-containing linear organopolysiloxane; a non-functional linear organopolysiloxane; and a silicate resin; wherein the dynamic viscosity of the non-functional linear organopolysiloxane at 25° C. is 100,000 mm²/sec or greater. The silicone pressure-sensitive adhesive has enhanced adhesion while minimizing skin damage and pain during removal of the adhesive.

17 Claims, 1 Drawing Sheet

(51) Int. Cl.
  *C08G 77/00* (2006.01)
  *C08G 77/08* (2006.01)
  *C08G 77/12* (2006.01)
  *C08G 77/16* (2006.01)
  *C08G 77/20* (2006.01)
  *C09J 7/38* (2018.01)
  *C09J 183/04* (2006.01)

(52) U.S. Cl.
  CPC .............. *C08G 77/16* (2013.01); *C08G 77/20* (2013.01); *C08G 77/70* (2013.01); *C09J 7/38* (2018.01); *C09J 2301/122* (2020.08); *C09J 2301/302* (2020.08)

(58) Field of Classification Search
  CPC ........ C08G 77/08; C08G 77/12; C08G 77/16; C08G 77/20; C08G 77/70; C08L 83/00; C08L 83/04
  USPC .................... 156/60, 64, 350, 351, 378, 379
  See application file for complete search history.

(56) References Cited

U.S. PATENT DOCUMENTS

| | | |
|---|---|---|
| 5,371,128 A | 12/1994 | Ulman |
| 8,541,481 B2 | 9/2013 | Determan |
| 2018/0133360 A1 | 5/2018 | Bingol |

FOREIGN PATENT DOCUMENTS

| | | |
|---|---|---|
| WO | WO 2010-056541 | 5/2010 |
| WO | WO 2010-056543 | 5/2010 |
| WO | WO 2010-056544 | 5/2010 |
| WO | 2012069794 A1 | 5/2012 |
| WO | WO 2014-093093 | 6/2014 |
| WO | WO 2016-173600 | 11/2016 |

OTHER PUBLICATIONS

International Search Report for PCT International Application No. PCT/IB2019/059631, dated Dec. 13, 2019, 4 pages.

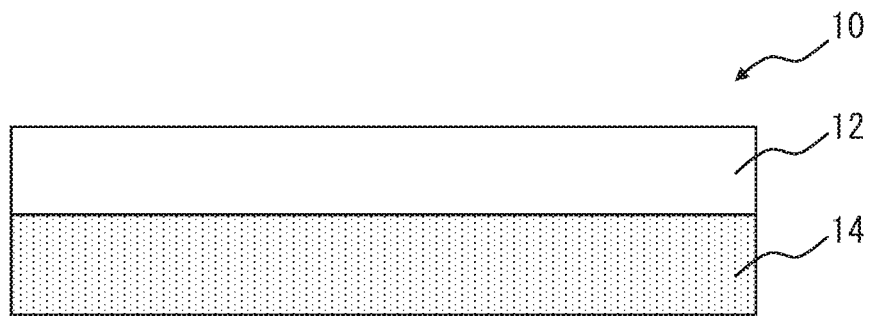

dynamic viscosity of the non-functional linear organopolysiloxane at 25° C. is 100,000 mm²/sec or greater.

According to further embodiment herein provided is a silicone pressure-sensitive adhesive composition, including a silanol end group-containing linear organopolysiloxane; a non-functional linear organopolysiloxane; and a silicate resin, wherein the dynamic viscosity of the non-functional linear organopolysiloxane at 25° C. is 100,000 mm²/sec or greater.

According to the present disclosure, silicone pressure-sensitive adhesives having an enhanced adhesion force while minimizing skin damage and pain during removal of the adhesive are provided.

SILICONE PRESSURE-SENSITIVE ADHESIVE AND SILICONE PRESSURE-SENSITIVE ADHESIVE COMPOSITION

CROSS REFERENCE TO RELATED APPLICATIONS

This application is a national stage filing under 35 U.S.C. 371 of PCT/I132019/059631, filed Nov. 8, 2019, which claims the benefit of Japanese Application No. 2018-214906, filed Nov. 15, 2018, the disclosure of which is incorporated by reference in its/their entirety herein.

TECHNICAL FIELD

The present disclosure relates to a silicone pressure-sensitive adhesive and a silicone pressure-sensitive adhesive composition.

BACKGROUND ART

Silicone pressure-sensitive adhesives have been used in various applications including medical applications. Medical silicone pressure-sensitive adhesives applied to skin desirably have an adhesive force for easily applying to skin at room temperature and sufficient holding force for fixing to skin for a predetermined period, and then the medical silicone pressure-sensitive adhesive can desirably be removed from skin without peeling skin and inducing pain.

Patent Document 1 (JP H05-86351A) describes "(1) from about 40 to about 70 parts by weight of a silicone resin; (2) from about 30 to about 60 parts by weight of a silicone fluid; and (3) from about 0.5 to about 20 parts by weight of a phenyl group-containing polysiloxane fluid (the viscosity is from 5 to 600 centistokes at 25° C.) for example, a mixture of $(CH_3)_3SiO[Si(C_6H_5)(OSi(CH_3)_3)O]_nSi(CH_3)_3$, provided that the sum amount of (1) and (2) is considered as 100 parts by weight."

Patent Document 2 (JP 2012-507608A) describes "an adhesive comprising a radiation cured silicone gel, the silicone gel comprising a cross-linked polydiorganosiloxane".

SUMMARY

In critical care applications, for example, critical tools such as cardiovascular catheters or urinary catheters or semi-critical tools such as endotracheal tubes, are required to be more securely fixed.

The present disclosure provides a silicone pressure-sensitive adhesive having an enhanced adhesion force while minimizing skin damage and pain during removal of the adhesive.

In some embodiments herein provided is a silicone pressure-sensitive adhesive, including the reaction product of a composition including a silanol end group-containing linear organopolysiloxane; a non-functional linear organopolysiloxane; and a silicate resin, wherein the dynamic viscosity of the non-functional linear organopolysiloxane at 25° C. is 100,000 mm²/sec or greater.

According to other embodiments herein provided is a silicone pressure-sensitive adhesive, including the cured product of a composition including an end-capped linear organopolysiloxane with silicate resin, which is a condensation product of a silanol end group-containing linear organopolysiloxane and a silicate resin; a non-functional linear organopolysiloxane; and a silicate resin, wherein the

BRIEF DESCRIPTION OF THE DRAWINGS

FIG. 1 is a schematic cross-sectional view of a medical product according to one embodiment of the present disclosure.

DETAILED DESCRIPTION

Although representative embodiments of the present disclosure will now be described in more detail for the purpose of illustration with reference to the drawings, the present disclosure is not limited to these embodiments.

The term "pressure-sensitive adhesiveness" as used herein means properties of a material or a composition having permanent adhesiveness within a range of the operation temperature, for example, within a range of 0° C. or higher and 50° C. or lower, being capable of adhering to various surfaces on a light force without changing the phase (from liquid to solid).

The term "silicone pressure-sensitive adhesive" as used herein means a material having pressure-sensitive adhesiveness and being capable of having various shapes including a layer, a spot, a line, a pattern, and a foam.

The term "silicone pressure-sensitive adhesive composition" as used herein means a mixture of materials being capable of forming the silicone pressure-sensitive adhesive by electron beam irradiation, gamma ray irradiation, oxidation using a peroxide, or curing by a hydrosilylation addition reaction. The silicone pressure-sensitive adhesive composition may or may not exhibit pressure-sensitive adhesiveness.

The term "non-functional" as used herein means that the organopolysiloxane does not have a functional group exhibiting reactivity or polymerizable reactivity with another functional group including a hydroxyl group, a silanol group, a Si—H group, a vinyl group, an allyl group, an acrylic group, a methacrylic group, an epoxy group, an amino group, and a mercapto group. Examples of non-functional groups include an alkyl group or an aryl group consisting of a carbon, a hydrogen, and in some embodiments, a halogen atom (for example, a fluorine atom).

The organopolysiloxane has various forms including liquids (fluids), oils, gums, elastomers, or resins (for example, crushable solids). Generally, materials having low molecular weight and low viscosity are referred to as fluids or oils, and materials having higher molecular weight and higher viscosity are referred to as gums. However, the two terms have no clear differentiation. Elastomers and resins have higher molecular weight than gums, and they typically do not flow. The terms "liquids (fluids)" and "oils" as used herein refers to a material having a viscosity of 1,000,000 mm²/sec or less at 25° C. The "gums" as used herein means a material having a viscosity of 1,000,000 mm²/sec or greater at 25° C.

In the present disclosure, the dynamic viscosity of the organopolysiloxane is measured by using an Ubbelohde viscometer. In the case where the dynamic viscosity is greater than the upper limit as measured by the Ubbelohde viscometer, the viscosity can be measured by a circular cone-plate type rotating viscometer. As the circular cone-plate type rotating viscometer measuring at the constant speed of the plate, for example, a dynamic viscoelasticity measuring apparatus ARES manufactured by TA Instruments can be used. In the dimension of the viscometer, the diameter of the circular plate is 25 mm, and the angle between the circular cone and the circular plate α is set to be 0.1 radian. The dynamic viscosity is a value (in mm²/sec) obtained by dividing the viscosity (in mPa·s) of the organopolysiloxane measured at a shear speed of 0.1 sec⁻¹ at 25° C. by the density of the organopolysiloxane.

The silicone pressure-sensitive adhesive according to a first embodiment includes the reaction product of a composition including a silanol end group-containing linear organopolysiloxane; a non-functional linear organopolysiloxane; and a silicate resin. The dynamic viscosity of the non-functional linear organopolysiloxane at 25° C. is about 100,000 mm²/sec (about 100,000 centistokes) or greater.

The reaction product of the composition including the silanol end group-containing linear organopolysiloxane; the non-functional linear organopolysiloxane; and the silicate resin includes an end-capped linear organopolysiloxane with the silicate resin, which is a condensation product of a silanol end group-containing linear organopolysiloxane and a silicate resin. Since the silicone pressure-sensitive adhesive includes the end-capped linear organopolysiloxane with the silicate resin, the silicone pressure-sensitive adhesive can have enhanced adhesive force compared to the corresponding silicone pressure-sensitive adhesive including a silicate resin besides the end-capped linear organopolysiloxane with the silicate resin.

Further, the reaction product may contain cross-linking formed by reacting radicals of the organic side chain group in the silanol end group-containing linear organopolysiloxane, the non-functional linear organopolysiloxane or the end-capped linear organopolysiloxane with the silicate resin. Alternatively, the reaction product may contain cross-linking obtained by hydrosilylation of the silanol end group-containing linear organopolysiloxane further having an alkenyl group, the silicate resin, or the end-capped linear organopolysiloxane with the silicate resin with the organohydrogen polysiloxane. Because of the cross-linking, the cured product has sufficient cohesive force as a silicone pressure-sensitive adhesive.

The silicone pressure-sensitive adhesive according to a second embodiment includes a cured product of a composition comprising an end-capped linear organopolysiloxane with the silicate resin, which is a condensation product of a silanol end group-containing linear organopolysiloxane and a silicate resin; a non-functional linear organopolysiloxane; and a silicate resin. The dynamic viscosity of the non-functional linear organopolysiloxane at 25° C. is about 100,000 mm²/sec (about 100,000 centistokes) or greater. Since the silicone pressure-sensitive adhesive includes the end-capped linear organopolysiloxane with the silicate resin, the silicone pressure-sensitive adhesive can have enhanced adhesive force compared to the corresponding silicone pressure-sensitive adhesive including a silicate resin besides the end-capped linear organopolysiloxane with the silicate resin.

The cured product may contain cross-linking formed by reacting radicals of the organic side chain group in the end-capped linear organopolysiloxane with the silicate resin or the non-functional linear organopolysiloxane. Alternatively, the cured product may contain cross-linking obtained by hydrosilylation of the silanol end group-containing linear organopolysiloxane further having an alkenyl group or the silicate resin with the silicate resin with the organohydrogen polysiloxane. Because of the cross-linking, the cured product has sufficient cohesive force as a silicone pressure-sensitive adhesive.

The silanol end group-containing linear organopolysiloxane contains a polysiloxane main chain having an organic side chain group and has a silanol group at one end or both ends. The silanol end group-containing linear organopolysiloxane is involved in the formation of the condensation product with silicate resin. The presence of the condensation product is involved in improving the adhesive force of the silicone pressure-sensitive adhesive.

In some embodiments, the silanol end group-containing linear organopolysiloxane is represented by Formula (1):

Formula 1

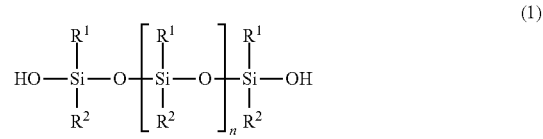

(1)

In Formula (1), each $R^1$ and $R^2$ is independently an aliphatic hydrocarbon group having 1 to 6 carbon atoms or a phenyl group; a plurality of $R^1$ s may be identical or different from each other; a plurality of R e s may be identical or different from each other; and n is an integer of 1 or greater. For example, n may be a value such that the dynamic viscosity of the silanol end group-containing linear organopolysiloxane at 25° C. is about 500 mm²/sec or greater, about 1000 mm²/sec or greater, or about 2000 mm²/sec or greater, and about 2,000,000 mm²/sec or less, about 1,000,000 mm²/sec or less, or about 500,000 mm²/sec or less.

Examples of aliphatic hydrocarbon groups having 1 to 6 carbon atoms are alkyl groups including a methyl group, an ethyl group, an n-propyl group, an isopropyl group, an n-butyl group, and an n-hexyl group; a cycloalkyl group including a cyclohexyl group; and an alkenyl group including a vinyl group, an allyl group, and a hexenyl group. The aliphatic hydrocarbon group having 1 to 6 carbon atoms and the phenyl group may have a halogen substituent, for example, a fluorine. Examples of aliphatic hydrocarbon group having 1 to 6 carbon atoms and a phenyl group having a halogen substituent include a —CH₂CH₂CF₃ group, a —CH₂CH₂C₄F₉ group, and a pentafluorophenyl group.

In some embodiments, $R^1$ and $R^2$ in Formula (1) is an alkyl group including a methyl group, an ethyl group, an n-propyl group, an isopropyl group, an n-butyl group, and an n-hexyl group, in particular, a methyl group. The silanol end group-containing linear organopolysiloxane in which $R^1$ and $R^2$ in Formula (1) is a methyl group is a silanol end group-containing linear polydimethylsiloxane. Since the silanol end group-containing linear polydimethylsiloxane forms a relatively soft cured product, a silicone pressure-sensitive adhesive which is gentle for skin can be obtained.

The dynamic viscosity of the silanol end group-containing linear organopolysiloxane at 25° C. can be generally about 500 mm²/sec or greater, about 1000 mm²/sec or greater, or about 2000 mm²/sec or greater, and about 2,000,000 mm²/sec or less, about 1,000,000 mm²/sec or less, or about 500,000 mm²/sec or less.

In one embodiment, the amount of silanol end group-containing linear organopolysiloxane is about 5 parts by weight or greater, about 10 parts by weight or greater, or about 15 parts by weight or greater, and about 35 parts by weight or less, about 30 parts by weight or less, or about 25 parts by weight or less based on 100 parts by weight of the solid content of the silicone pressure-sensitive adhesive. The amount of silanol end group-containing linear organopolysiloxane, as used herein, means the total amount of the unreacted or free silanol end group-containing linear organopolysiloxane and the silanol end group-containing linear organopolysiloxane in the end-capped linear organopolysiloxane with the silicate resin.

The non-functional linear organopolysiloxane is an ingredient providing mild peeling from skin. Although the non-functional linear organopolysiloxane may form cross-links formed by reacting radicals of its organic side chain groups, the unreacted non-functional linear organopolysiloxane remains as a plasticizer and can provide gentle removal properties from skin while minimizing skin damage and pain from the silicone pressure-sensitive adhesive. Since the non-functional linear organopolysiloxane is a fluid or a gum having high dynamic viscosity of about 1,000,000 mm²/sec or greater at 25° C., that is high molecular weight non-functional linear organopolysiloxane. Even if the organopolysiloxane is unreacted, the organopolysiloxane has difficulty bleeding out from the surface of the pressure-sensitive adhesive due to the entanglement with the cross-linked polymer matrix and does not decrease the adhesive force to skin excessively. Therefore, the pressure-sensitive adhesive of the present disclosure can have a balance of high adhesive force to skin and gentle removal properties from skin, a trade-off relationship as understood by a person skilled in the art.

In some embodiments, the dynamic viscosity of the non-functional linear organopolysiloxane at 25° C. is about 100,000 mm²/sec or greater, about 150,000 mm²/sec or greater, or about 200,000 mm²/sec or greater, and about 1,000,0000 mm²/sec or less, or about 5,000,000 mm²/sec or less.

In some embodiments, the non-functional linear organopolysiloxane is represented by Formula (2):

Formula 2

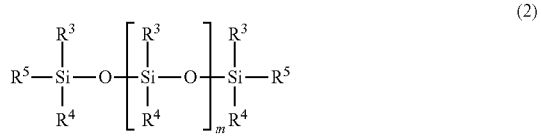

(2)

In Formula (2), each $R^3$, $R^4$ and $R^5$ is independently an alkyl group having 1 to 6 carbon atoms or a phenyl group; a plurality of R a s may be identical or different from each other; a plurality of $R^4$s may be identical or different from each other; a plurality of $R^5$ s may be identical or different from each other; and m is an integer of 1 or greater. For example, m may be a value such that the dynamic viscosity of the non-functional linear organopolysiloxane at 25° C. is about 100,000 mm²/sec or greater, about 150,000 mm²/sec or greater, or about 200,000 mm²/sec or greater, and about 1,000,0000 mm²/sec or less, or about 500,000 mm²/sec or less.

Examples of alkyl groups having 1 to 6 carbon atoms include a methyl group, an ethyl group, an n-propyl group, an isopropyl group, an n-butyl group, and an n-hexyl group. The alkyl group having 1 to 6 carbon atoms and the phenyl group may have a halogen substituent, for example, a fluorine. Examples of alkyl groups having 1 to 6 carbon atoms and a phenyl group having a halogen substituent include a —$CH_2CH_2CF_3$ group, a —$CH_2CH_2C_4F_9$ group, and a pentafluorophenyl group.

In some embodiments, each $R^3$, $R^4$ and $R^5$ in Formula (2) is a methyl group. The non-functional linear organopolysiloxane in which each $R^3$, $R^4$ and $R^5$ in Formula (2) is a methyl group is a trimethylsilyl end group-containing linear polydimethylsiloxane. Since trimethylsilyl end group-containing linear polydimethylsiloxane forms a relatively soft cured product, a silicone pressure-sensitive adhesive which is gentle to skin can be obtained.

In some embodiments, the amount of the non-functional linear organopolysiloxane is about 25 parts by weight or greater, about 30 parts by weight or greater, or about 40 parts by weight or greater, and about 60 parts by weight or less, about 55 parts by weight or less, or about 50 parts by weight or less based on 100 parts by weight of the solid content of the silicone pressure-sensitive adhesive.

The silicate resin serves as a tackifier for the silicone pressure-sensitive adhesive. Further, the silicate resin is involved in the formation of the condensation product with the silanol end group-containing linear organopolysiloxane. The presence of the condensation product is involved in improving the adhesive force of the silicone pressure-sensitive adhesive.

The silicate resin is generally a solid polysiloxane having a three-dimensional network structure containing a structure unit T (trivalent $RSiO_{3/2}$ unit), a structure unit Q (tetravalent $SiO_{4/2}$ unit), or combination thereof, and optionally having a structure unit M (monovalent $R^3SiO_{1/2}$ unit) and a structure unit D (divalent $R^2SiO_{2/2}$ unit), or combination thereof. The M unit caps the end of the silicate resin. Examples of silicate resin include an MQ resin, an MDQ resin, an MTQ resin, and an MDTQ resin. One silicate resin can be used, or two or more silicate resins may be used in combination.

Each organic group R in the silicate resin is independently an aliphatic hydrocarbon group having 1 to 6 carbon atoms or a phenyl group; and a plurality of Rs may be identical or different from each other. Examples of aliphatic hydrocarbon groups having 1 to 6 carbon atoms are an alkyl groups including a methyl group, an ethyl group, an n-propyl group, an isopropyl group, an n-butyl group, and an n-hexyl group; a cycloalkyl group including a cyclohexyl group; and an alkenyl group including a vinyl group, an allyl group, and a hexenyl group. The aliphatic hydrocarbon group having 1 to 6 carbon atoms and the phenyl group may have a halogen substituent, for example, a fluorine. Examples of aliphatic hydrocarbon groups having 1 to 6 carbon atoms and a phenyl group having a halogen substituent include a —$CH_2CH_2CF_3$ group, a —$CH_2CH_2C_4F_9$ group, and a pentafluorophenyl group.

In some embodiments, about 90% or greater, about 95% or greater, or 100% of the organic groups R in the silicate resin are methyl groups.

In some embodiments, a part of the organic group R in the silicate resin is an alkenyl group including a vinyl group, an allyl group, and a hexenyl group, in particular, a vinyl group. The silicate resin having an alkenyl group can form cross-links by a hydrosilylation addition reaction in combination with a organohydrogen polysiloxane and a hydrosilylation catalyst. In this embodiment, all of the remaining organic groups R may be methyl groups.

In some embodiments, the silicate resin is an MQ resin. In the MQ resin, each M unit is connected to the Q unit, each Q unit is connected to at least one of another Q unit, and a part of the Q unit is only connected to the other Q unit. The ratio of the number of M unit/Q unit of the MQ resin is generally about 0.3 or greater, about 0.4 or greater, or about 0.5 or greater, and about 1.7 or less, about 1.5 or less, or about 1.3 or less. When the ratio of the number of M unit/Q unit is about 0.3 or greater, sufficient adhesive force and sufficient initial adhesive force (tack) can be obtained. When the ratio is about 1.7 or less, sufficient adhesive force and holding force can be obtained.

The silicate resin comprises HO—$SiO_{3/2}$ unit (Toll unit), HO—$RSiO_{2/2}$ unit (DOH unit), or HO—$R^2SiO_{1/2}$ ($M_{OH}$ unit) in which a part of silicon atom in the Q unit, T unit or optional D unit is connected to a hydroxyl group. That is, a part of the organic group R in the silicate resin is substituted with an OH group. The OH group (silanol group) of these $T_{OH}$ unit, $D_{OH}$ unit and $M_{OH}$ unit is condensed with the silanol group of the silanol end group-containing linear organopolysiloxane to form the end-capped linear organopolysiloxane with the silicate resin.

The concentration of the silanol group in the silicate resin can be generally about 0.01 weight % or greater, about 0.02 weight % or greater, about 0.05 weight % or greater, or about 0.1 weight % or greater, and about 1.5 weight % or less, about 1.2 weight % or less, about 1.0 weight % or less, or about 0.8 weight % or less based on the weight of the silicate resin. When the concentration of silanol groups of the silicate resin is about 0.01 weight % or greater, the end-capped linear organopolysiloxane with the silicate resin can be formed to the sufficient extent that the adhesive force of the silicone pressure-sensitive adhesive is increased. When the concentration of silanol groups of the silicate resin is about 1.5 weight % or less, the initial adhesive force (tack) of the silicone pressure-sensitive adhesive can be increased.

In general, the silicate resin has a number average molecular weight of about 100 g/mol or greater, or about 500 g/mol or greater, and about 50,000 g/mol or less, or about 15,000 g/mol or less.

In some embodiments, the amount of the silicate resin is about 30 parts by weight or greater, about 35 parts by weight or greater, or about 40 parts by weight or greater, and about 65 parts by weight or less, about 60 parts by weight or less, or about 55 parts by weight or less based on 100 parts by weight of the solid content of the silicone pressure-sensitive adhesive. The amount of the silicate resin, as used herein, means a total amount of the unreacted or free silicate resin and the silicate resin portion in the end-capped linear organopolysiloxane with the silicate resin.

In a first embodiment, the molar equivalent of a silanol group in the silicate resin may be greater than that of a silanol group in the silanol end group-containing linear organopolysiloxane. In this embodiment, the unreacted silicate resin remains after the condensation reaction of the silicate resin and the silanol end group-containing linear organopolysiloxane. The unreacted silicate resin can corporate with the end-capped linear organopolysiloxane with the silicate resin formed by the condensation reaction to provide high adhesive force to the silicone pressure-sensitive adhesive.

In some embodiments, substantively all of, for example, about 95% or greater, about 98% or greater, or about 99% or greater, or all of the end of the silanol end group-containing linear organopolysiloxane may be capped with the silicate resin.

The end-capped linear organopolysiloxane with the silicate resin may be produced by the condensation reaction of the silanol end group-containing linear organopolysiloxane and the silicate resin. The condensation reaction can be generally carried out by using a base catalyst. Examples of base catalysts include a metal hydroxide including lithium hydroxide, sodium hydroxide, potassium hydroxide, and calcium hydroxide; a carbonate salt including sodium carbonate and potassium carbonate; a bicarbonate salt including sodium bicarbonate; a metal alkoxide including sodium methoxide or potassium butoxide; an organic metal including butyl lithium; a complex of potassium hydroxide and a siloxane; a nitrogen compound including ammonia gas, aqueous ammonia solution, methylamine, trimethylamine, and triethylamine. Since the catalyst can be easily removed by using reduced pressure stripping, ammonia gas or aqueous ammonia solution is advantageously used as the base catalyst.

The condensation reaction may be carried out in the presence of a solvent or in the absence of a solvent. Examples of suitable solvents include an aromatic hydrocarbon including toluene and xylene; a linear or branched aliphatic hydrocarbon including hexane, heptane, octane, isooctane, decane, cyclohexane, methylcyclohexane, and isoparaffin; a hydrocarbon-based solvent including industrial gasoline, petroleum benzine, and solvent naphtha; a ketone including acetone, methyl ethyl ketone, 2-pentanone, 3-pentanone, 2-hexanone, 2-heptanone, 4-heptanone, methyl isobutyl ketone, diisobutyl ketone, acetonyl acetone, and cyclohexanone; an ester including ethyl acetate, propyl acetate, isopropyl acetate, butyl acetate, and isobutyl acetate; an ether including diethylether, dipropylether, diisopropylether, dibutylether, 1,2-dimethoxyethane, and 1,4-dioxane; an acetate solvent including 2-methyoxyethyl acetate, 2-ethyoxyethyl acetate, propylene glycol monomethylether acatate, and 2-butoxyethyl acetate; or a mixed solvent thereof. In some embodiments, the solvent is an aromatic hydrocarbon, a linear or branched alphatic hydrocarbon, or a mixed solvent of a linear or branched alphatic hydrocarbon and an ether, an ester, or an acetate solvent.

In cases where the condensation reaction is carried out in the absence of the solvent, the non-functional linear organopolysiloxane may also be included. When the non-functional linear organopolysiloxane is also included, excessive thickening or gelation from the condensation reaction of the silicate resin and the silanol end group-containing linear organopolysiloxane can be prevented.

The temperature of the condensation reaction can be generally about 20° C. or higher, about 30° C. or higher, or about 40° C. or higher, and about 150° C. or lower, about 110° C. or lower, or about 80° C. or lower. The condensation reaction may be carried out at the reflux temperature of the optional solvent.

The condensation reaction can be carried out until about 90% or greater, about 95% or greater, or about 98% or greater of the silanol group in the silanol end group-containing linear organopolysiloxane is reacted. In some embodiments, substantially all of the silanol group of the silanol end group-containing linear organopolysiloxane is consumed to the condensation reaction with the silicate resin by using an excess molar equivalent of the silicate.

Although the time of the condensation reaction is not particularly limited, the time is generally about 0.5 hour or more, or about 1 hour or more, and about 48 hours or less, or about 24 hours or less.

After the condensation reaction, a neutralizer for neutralizing the base catalyst may be added, as needed. Examples of the neutralizer include an acidic gas including hydrogen chloride and carbon dioxide; an organic acid including octylic acid and citric acid; a mineral acid including hydrochloric acid, sulfuric acid and phosphoric acid. In addition to the neutralization, or instead of the neutralization, the base catalyst can be removed by reduced pressure stripping or washing with water.

In some embodiments, the silicone pressure-sensitive adhesive contains cross-linking formed by reacting radicals of the organic side chain groups of the silanol end group-containing linear organopolysiloxane, the non-functional linear organopolysiloxane, or the end-capped linear organopolysiloxane with the silicate resin. In these embodiments, the non-functional linear organopolysiloxane may be cross-linked via its organic side chain group. For example, when the organic side chain group is a methyl group, electron beam irradiation, gamma ray irradiation, or a radical generated from the decomposition of an organic peroxide, abstracts a hydrogen radical from the methyl group to form a methylene radical. The methylene radical is re-coupled with another methylene radical to form a linking structure —Si—CH$_2$—CH$_2$—Si-between polysiloxane main chains. The end-capped linear organopolysiloxane with the silicate resin can enhance the cohesive force of the resulting cured product effectively, even if cross-linking is carried out by irradiating with a relatively low dose of electron beam or gamma ray radiation. Therefore, high adhesive force and gentle removal from skin can be achieved.

The electron beam irradiation or the gamma ray irradiation can be carried out by using a known electron beam irradiation apparatus or gamma ray irradiation apparatus, known irradiation conditions and known irradiation procedures. Electron beam irradiation and gamma ray irradiation may be done in combination. Electron beam irradiation or gamma ray irradiation may be carried out once, or a plurality of irradiations may be carried out by changing the irradiation orientation of the object to be irradiated. The electron beam irradiation or the gamma ray irradiation may be carried out under inert gas atmosphere (for example, nitrogen or argon). After the object to be irradiated is covered with a liner and blocked from air, the electron beam irradiation or the gamma ray irradiation may be carried out through the liner. A semi-finished product and a product such as a tape or a wound dressing can be simultaneously sterilized with a gamma ray irradiation apparatus.

The dose of electron beam irradiation can be about 0.5 Mrad or greater, about 0.8 Mrad or greater, or about 1.0 Mrad or greater, and about 15 Mrad or less, about 12 Mrad or less, or about 10 Mrad or less, for example. In a case where the non-functional linear organopolysiloxane has high molecular weight, that is, high dynamic viscosity, the amount of the non-functional linear organopolysiloxane which can be transferred to skin may be increased by irradiating with a relatively low absorbed dose and decreasing the amount of the formed cross-linking.

The accelerating voltage of the electron beam irradiation can be suitably selected depending on the thickness of the pressure-sensitive adhesive and the presence or absence of a liner. For example, the accelerating voltage can be about 80 keV or greater, about 100 keV or greater, or about 140 keV or greater, and about 500 keV or less, about 300 keV or less, or about 250 keV or less.

As the source of the gamma ray irradiation, Cobalt 60 (60 Co) can be generally used. The absorbed dose of the gamma ray irradiation can be suitably selected depending on the thickness of the pressure-sensitive adhesive or the presence or absence of a liner. In the case where the non-functional linear organopolysiloxane has high molecular weight, that is, high dynamic viscosity, the amount of the non-functional linear organopolysiloxane which can be transferred to skin may be increased by irradiating with a relatively low absorbed dose and decreasing the amount of the formed cross-linking.

Examples of organic peroxides which can be used include dibenzoyl peroxide, 4,4'-dimethyl dibenzoyl peroxide, 3,3'-dimethyl dibenzoyl peroxide, 2,2'-dimethyl dibenzoyl peroxide, 2,2',4,4'-tetrachlorodibenzoyl peroxide, and cumyl peroxide. One organic peroxide can be used, or two or more organic peroxides may be used in combination.

The form of the organic peroxide is not particularly limited. The organic peroxide can be used as it is, or may be diluted with a solvent, or may be dispersed in water. Alternatively, the organic peroxide may be dispersed with the silanol end group-containing linear organopolysiloxane or the non-functional linear organopolysiloxane to form a paste.

The amount of the organic peroxide can be suitably determined depending on the curing temperature and the decomposition temperature of the organic peroxide used. The amount of the organic peroxide is generally about 0.5 parts by weight or more, or about 0.8 parts by weight or more, and about 5 parts by weight or less, or about 3 parts by weight or less based on 100 parts by weight of the solid content of the silicone pressure-sensitive adhesive.

In a second embodiment, the silicone pressure-sensitive adhesive contains cross-links from hydrosilylation of: the silanol end group-containing linear organopolysiloxane having an alkenyl group such as a vinyl group, an allyl group and a hexenyl group, the silicate resin, or the end-capped linear organopolysiloxane with the silicate resin; and an organohydrogen polysiloxane. The alkenyl group is reacted with the organohydrogen polysiloxane described below by the addition reaction to form cross-links and producing the cured product which is a component of the silicone pressure-sensitive adhesive.

In addition to the silanol end group-containing linear organopolysiloxane further having an alkenyl group, the silicate resin, or the end-capped linear organopolysiloxane with the silicate resin, the linear organopolysiloxane represented by Formula (3) may be used.

Formula 3

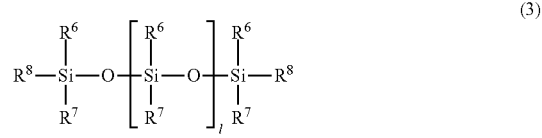

(3)

In Formula (3), each $R^6$, $R^7$, and $R^8$ is independently an aliphatic hydrocarbon group having 1 to 6 carbon atoms or a phenyl group; a plurality of $R^6$ s may be identical or different from each other; a plurality of Ies may be identical or different from each other; a plurality of $R^8$ s may be identical or different from each other; provided that at least one of all substituents represented by $R^6$, $R^7$, and $R^8$ is an alkenyl group; and l is an integer of 1 or more. For example, l may be a value such that the dynamic viscosity of the linear organopolysiloxane represented by Formula (3) at 25° C. is about 500 mm²/sec or greater, about 1000 mm²/sec or greater, or about 2000 mm²/sec or greater, and about 2,000,000 mm²/sec or less, about 1,000,000 mm²/sec or less, or about 500,000 mm²/sec or less.

Examples of aliphatic hydrocarbon groups having 1 to 6 carbon atoms include an alkyl group including a methyl group, an ethyl group, an n-propyl group, an isopropyl group, an n-butyl group, and an n-hexyl group; a cycloalkyl group including a cyclohexyl group; and an alkenyl group including a vinyl group, an allyl group, a hexenyl group, and an octenyl group. The aliphatic hydrocarbon group having 1 to 6 carbon atoms and the phenyl group may have a halogen substituent, for example, a fluorine. Examples of aliphatic hydrocarbon groups having 1 to 6 carbon atoms and a phenyl group having halogen substitution include a —$CH_2CH_2CF_3$ group, a —$CH_2CH_2C_4F_9$ group, and a pentafluorophenyl group.

The amount of linear organopolysiloxane represented by Formula (3) utilized can be about 0 parts by weight or greater, about 2 parts by weight or greater, or about parts by weight or greater, and about 30 parts by weight or less, about 20 parts by weight or less, or about 15 parts by weight or less based on 100 parts by weight of the solid content of the silicone pressure-sensitive adhesive.

An organohydrogen polysiloxane has three or more Si—H groups and serves as a cross-linking agent by hydrosilylation. The organohydrogen polysiloxane may be linear or branched.

In some embodiments, the organohydrogen polysiloxane is represented by Formula (4) or Formula (5):

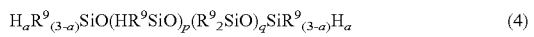

Formula 4

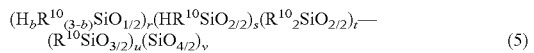

Formula 5

In Formula (4), each $R^9$ is independently an alkyl group having 1 to 6 carbon atoms or a phenyl group; a plurality of $R^9$ s may be identical or different from each other; a is 0 or 1; p is an integer of 1 or greater; q is an integer of 1 or greater; and when a is 0, p is an integer of 3 or greater, and p+q is an integer of 1 or greater. For example, p+q may be about 10 or greater, about 20 or greater, or about 50 or greater, and about 10000 or less, about 5000 or less, or about 2000 or less.

In Formula (5), each $R^{10}$ is independently an alkyl group having 1 to 6 carbon atoms or a phenyl group; a plurality of $R^{10}$s may be identical or different from each other; b is 0 or 1; r is an integer from 3 to 12; s is an integer of 0 or greater; t is an integer of 0 or greater; u+v is an integer from 1 to 5; and r+s+t+u+v is an integer of 4 or greater. For example, r+s+t+u+v may be about 10 or greater, about 20 or greater, or about 50 or greater, and about 10,000 or less, about 5000 or less, or about 2000 or less.

Examples of the alkyl group having 1 to 6 carbon atoms include a methyl group, an ethyl group, an n-propyl group, an isopropyl group, an n-butyl group, and an n-hexyl group. The alkyl group having 1 to 6 carbon atoms and the phenyl group may have a halogen substituent, for example, a fluorine. Examples of an alkyl group having 1 to 6 carbon atoms and a phenyl group having halogen substitution include a —$CH_2CH_2CF_3$ group, a —$CH_2CH_2C_4F_9$ group, and a pentafluorophenyl group.

The amount of the organohydrogen polysiloxane is generally adjusted so that the ratio of the number of Si—H groups to the total number of the alkenyl groups (the number of Si—H group/total number of the alkenyl group) is about 0.5 or greater, or about 0.8 or greater, and about 20 or less, or about 15 or less. When the ratio of the number of Si—H groups to the total number of the alkenyl groups is about 0.5 or greater, an adhesive with sufficient cohesive force and sufficient holding force can be obtained. When the ratio of the number of Si—H groups to the total number of the alkenyl groups is about 20 or less, the cohesive force and the holding force can be saturated, which is advantageous economically.

The cross-linking by hydrosilylation is carried out by using a catalyst. Examples of hydrosilylation catalysts include platinum-based catalysts, such as chloroplatinic acid, a solution of chloroplatinic acid in an alcohol, the reaction product of chloroplatinic acid and an alcohol, the reaction product of chloroplatinic acid and an olefin compound, the reaction product of chloroplatinic acid and a vinyl group-containing siloxane, platinum-olefin complexes, platinum-vinyl group-containing siloxane complexes; and platinum group-based catalysts, such as a rhodium complex and a ruthenium complex. The hydrosilylation catalysts may be used by dissolving or dispersing in a solvent such as isopropanol or toluene, or a silicone oil.

The amount of the hydrosilylation catalyst can be generally about 5 ppm or greater, or about 10 ppm or greater, and about 2,000 ppm or less, or about 500 ppm or less based on 100 parts by weight of the solid content of the silicone pressure-sensitive adhesive, as determined by the weight of platinum group metal.

An addition reaction controlling agent may be used in addition to the hydrosilylation catalyst. The addition reaction controlling agent controls the catalysis to prevent the composition from thickening or gelation before curing the silicone pressure-sensitive adhesive. Examples of addition reaction controlling agents include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyn, 3-methyl-3-trimethylsiloxy-1-pentyne, 3,5-dimethyl-3-trimethylsiloxy-1-hexyn, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, and 1,1,3,3-tetramethyl-1,3-divinylsiloxane.

The amount of the addition reaction controlling agent can be generally about 0.01 parts by weight or greater, or about 0.05 parts by weight or greater, and about 8.0 parts by weight or less, or about 2.0 parts by weight or less based on 100 parts by weight of the solid content of the silicone pressure-sensitive adhesive.

The silicone pressure-sensitive adhesive may include a drug such as an antibacterial agent, and an additive such as a filler, a microsphere (for example, expandable microsphere), a pigment, a dye, an adhesion improving agent, a cosmetic agent, a natural extract, a wax, a hydrophilic polymer, a water absorbing polymer, a moisturizer, and a rheology modifier.

In some embodiments, the silicone pressure-sensitive adhesive may include a non-functional linear organopolysiloxane having low viscosity, for example, a dynamic viscosity of about 100 mm²/sec to about 50,000 mm²/sec at 25° C. In these embodiments, the viscosity of the composition comprising the silanol end group-containing linear organopolysiloxane, the non-functional linear organopolysiloxane and the silicate resin, or the viscoelasticity and the wettability of the cured product which is the reaction product of the composition can be adjusted.

The silicone pressure-sensitive adhesive according to a first embodiment can be produced as follows. In the presence or absence of a solvent, to a solution or a mixture containing the reaction product obtained by the condensation reaction of the silanol end group-containing linear organopolysiloxane and the silicate resin is added a non-functional linear organopolysiloxane, and optional organic peroxide, a linear organopolysiloxane represented by Formula (3), an organohydrogen polysiloxane, a hydrosilylation catalyst, an addition reaction controlling agent, an additive, and a solvent, and mixed by using a planetary mixer, a blender, a mill, a roll, or an extruder. Alternatively, all or a part of a non-functional linear organopolysiloxane may also be presented in the condensation reaction of a silanol end group-containing linear organopolysiloxane and a silicate resin. The resulting pressure-sensitive adhesive composition was applied on a substrate such as a tape backing by using a bar coater, a hot melt coater, or an extruder, dried, i.e. the solvent was removed as needed, and cured by heating, electron beam irradiation, or gamma ray irradiation. In order to increase the viscosity of the pressure-sensitive adhesive composition and to prevent the gelation during operation, at least one of the organohydrogen polysiloxane and the hydrosilylation catalyst are preferably added immediately before curing.

The silicone pressure-sensitive adhesive according to a second embodiment can be produced as follows. An end-capped linear organopolysiloxane with the silicate resin which is a condensation product of the silanol end group-containing linear organopolysiloxane and the silicate resin, is prepared. The end-capped linear organopolysiloxane with the silicate resin, the non-functional linear organopolysiloxane and the silicate resin, an optional organic peroxide, a linear organopolysiloxane represented by Formula (3), an organohydrogen polysiloxane, a hydrosilylation catalyst, an addition reaction controlling agent, an additive, and a solvent are mixed. The resulting composition was applied on a substrate such as a tape backing by using a bar coater, a hot melt coater, or an extruder, dried i.e. the solvent was removed as needed, and cured by heating, electron beam irradiation, or gamma ray irradiation. All or a part of the silicate resin may remain in the unreacted state during the condensation reaction of the silanol end group-containing linear organopolysiloxane and the silicate resin.

In some embodiments, the silicone pressure-sensitive adhesive is essentially free of or free of a residue of a catalyst and a reaction initiator. The term "essentially free of" means that the residue of the catalyst and the reaction initiator contained in the silicone pressure-sensitive adhesive is about 0.1 weight % or less, about 0.05 weight % or less, or about 0.01 weight % or less, for example. Examples of catalyst residue include a hydrosilylation catalyst such as a platinum-based catalyst; and examples of the residue of a reaction initiator includes the degraded product of an organic peroxide.

The silicone pressure-sensitive adhesive composition according to a third embodiment includes a silanol end group-containing linear organopolysiloxane; a non-functional linear organopolysiloxane; and a silicate resin. The dynamic viscosity of the non-functional linear organopolysiloxane at 25° C. is about 100,000 mm$^2$/sec (about 100,000 centistokes) or greater. In the silicone pressure-sensitive adhesive composition according to this embodiment, the above-described silicone pressure-sensitive adhesive of the embodiment containing the end-capped linear organopolysiloxane with the silicate resin can be prepared by further carrying out the condensation reaction of the silanol end group-containing linear organopolysiloxane and the silicate resin.

The silicone pressure-sensitive adhesive composition may include an organic peroxide, a linear organopolysiloxane represented by Formula (3), an organohydrogen polysiloxane, a hydrosilylation catalyst, an addition reaction controlling agent, an additive, or a solvent, as optional ingredients. For the description and embodiments of the silanol end group-containing linear organopolysiloxane, the non-functional linear organopolysiloxane, the silicate resin, and other optional ingredients such as an organic peroxide, a linear organopolysiloxane represented by Formula (3), an organohydrogen polysiloxane, a hydrosilylation catalyst, an addition reaction controlling agent, an additive, or a solvent are described above for forming the silicone pressure-sensitive adhesive of the first and the second embodiments.

The silicone pressure-sensitive adhesive composition may include the end-capped linear organopolysiloxane with the silicate resin which is the condensation product of the silanol end group-containing linear organopolysiloxane and the silicate resin. The end-capped linear organopolysiloxane with the silicate resin may be produced by the condensation reaction of the silanol end group-containing linear organopolysiloxane contained in the silicone pressure-sensitive adhesive composition and the silicate resin. Alternatively, the end-capped linear organopolysiloxane with the silicate resin may be separately synthesized, and then added.

In some embodiments, the silicone pressure-sensitive adhesive composition is essentially free of or free of a catalyst and a reaction initiator. The term "essentially free of" means that the residue of the catalyst or the reaction initiator contained in the silicone pressure-sensitive adhesive composition is about 0.1 weight % or less, about 0.05 weight % or less, or about 0.01 weight % or less. Examples of catalyst residue include a hydrosilylation catalyst such as a platinum-based catalyst; and examples of the residue of a reaction initiator includes the degraded product of an organic peroxide.

In some embodiments, the silicone pressure-sensitive adhesive composition further includes an organohydrogen polysiloxane and a hydrosilylation catalyst, and at least one of the silanol end group-containing linear organopolysiloxane and the silicate resin has an alkenyl group.

In some embodiments, the silicone pressure-sensitive adhesive is a medical pressure-sensitive adhesive which is gentle for skin. Since the silicone pressure-sensitive adhesive generally has lower surface tension compared to skin, the silicone pressure-sensitive adhesive can rapidly wet out on a wide range of surfaces. The silicone pressure-sensitive adhesive has a high deformation rate even if the adhesive is spread by low pressure, and has a viscoelasticity so as to provide the desired adhesiveness in terms of adhesive strength and bond duration. The non-functional linear organopolysiloxane, which is not involved in the cross-linking by radiation irradiation and remains in the unreacted state, and flows when the silicone pressure-sensitive adhesive is applied to skin, forms a thin film around the cross-linked silicone pressure-sensitive adhesive and skin and hair, and thereby the pain upon removing the silicone pressure-sensitive adhesive can be decreased. On the other hand, the presence of the unreacted non-functional linear organopolysiloxane keeps the elasticity of the silicone pressure-sensitive adhesive low. Therefore, during removal of the silicone pressure-sensitive adhesive, the peeling stress can be prevented from concentrating on the peeling line (the border line between the pressure-sensitive adhesive and skin), and the pain during peeling can be decreased by widely spreading the unreacted non-functional linear organopolysiloxane on the adhesive surface. Accordingly, when the high molecular weight non-functional linear organopolysiloxane is contained in the silicone pressure-sensitive adhesive, high adhesive force to skin and easily peeling from skin can be achieved simultaneously.

The silicone pressure-sensitive adhesive can be adhered between a substrate and a biological substrate (for example, human or an animal) by having the pressure-sensitive adhesive layer on the one surface of the substrate. In some embodiments, the silicone pressure-sensitive adhesive can be used advantageously for adhering medical substrates to the skin of a human and/or an animal.

Examples of medical substrates include polymeric materials, plastics, natural polymeric materials (for example, collagen, wood, cork, and leather), papers, woven fabrics and non-woven fabrics, metals, glasses, ceramics, and composites thereof.

The thickness of the pressure-sensitive adhesive layer is not particularly limited. In some embodiments, the thickness of the pressure-sensitive adhesive layer is about 10 μm or greater, about 20 μm or greater, or about 50 μm or greater, and about 2.0 mm or less, about 1.0 mm or less, or about 0.5 mm or less.

The schematic cross-sectional view of the medical product according to one embodiment is illustrated in FIG. 1. A medical product 10 includes a substrate 12 and a silicone pressure-sensitive adhesive 14 positioned on the first main surface of the substrate 12. In FIG. 1, the silicone pressure-sensitive adhesive is illustrated in the form of the pressure-sensitive adhesive layer. The opposite surface of the silicone pressure-sensitive adhesive 14 may be protected by a release liner. The medical product 10 can be windable upon itself. In this case, the exposed surface of the silicone pressure-sensitive adhesive 14 is contacted with the second main surface in which the silicone pressure-sensitive adhesive 14 is not positioned and opposite to the first main surface of the substrate 12. During use, the exposed surface of the silicone pressure-sensitive adhesive 14 is applied to the biological substrate (for example, skin of human) to adhere the substrate 12 to the biological substrate. A medical product can be fixed to the biological substrate by positioning the medical product such as a tube between the silicone pressure-sensitive adhesive 14 and the biological substrate, as needed. The silicone pressure-sensitive adhesive and the silicone pressure-sensitive adhesive composition can be used for medical products, for example, a tape, a wound dressing, a surgical drape, an IV portion dressing, an artificial limb, an ostomy pouch or a stroma pouch, a buccal pouch, or a transdermal patch. Further, other medical products such as artificial teeth and hair pieces can also use the product. The silicone pressure-sensitive adhesive and the silicone pressure-sensitive adhesive composition can be suitably used for critical care tapes and sheets in which high adhesive force and gently peeling properties from skin are required.

EXAMPLES

Although the illustrative embodiments of the present disclosure will be exemplified in the following examples, the present disclosure is not limited to these embodiments. All parts and percentages are based on the weight, unless otherwise stated.

The reagents and materials used in the examples are shown in Table 1.

TABLE 1

| Trade Name [1] | Description | Suppliers |
|---|---|---|
| KR-100 | Peroxide curable silicone pressure-sensitive adhesive (58 parts by weight of the hydroxyl group-containing MQ resin (M/Q = 0.69), 42 parts by weight of silanol end group-containing linear PDMS fluid, containing the condensation product of the MQ resin and the silanol end group-containing linear PDMS) toluene/xylene solution, the solid content is 60 weight % | Shin-Etsu Chemical Co., Ltd (Chiyoda-ku, Tokyo, Japan) |
| KF-96H-100 cs (KF-96 H-1M) | Trimethylsilyl end group-containing linear PDMS, the fluid viscosity is 1000000 cSt (25° C.) | Shin-Etsu Chemical Co., Ltd (Chiyoda-ku, Tokyo, Japan) |
| AK1,000,000 (AK 1 M) | Trimethylsilyl end group-containing linear PDMS, the fluid viscosity is 1,000,000 cSt (25° C.) | Wacker Asahikasei Silicone co., ltd. (Chiyoda-ku, Tokyo, Japan) |
| KF-96 H-30 cs (KF-96 H-0.3 M) | −30 FI cs (KF-96 H-Otrimethylsilyl end group-containing linear PDMS, the fluid viscosity is 300000 cSt (25° C.) | Shin-Etsu Chemical Co., Ltd (Chiyoda-ku, Tokyo, Japan) |
| AK 60,000 (AK 60 K) | Trimethylsilyl end group-containing linear PDMS, the fluid viscosity is 60000 cSt (25° C.) | Wacker Asahikasei Silicone co., ltd. (Chiyoda-ku, Tokyo, Japan) |
| MQ 803 TF | Hydroxyl group-containing MQ resin (M/Q = 0.56) | Wacker Asahikasei Silicone co., ltd. (Chiyoda-ku, Tokyo, Japan) |
| Elastomer 350 N | Silanol end group-containing linear PDMS, the viscosity is about 309000 cSt (25° C.) | Wacker Asahikasei Silicone co., ltd. (Chiyoda-ku, Tokyo, Japan) |

TABLE 1-continued

| Trade Name [1] | Description | Suppliers |
|---|---|---|
| YF3802 | Silanol end group-containing linear PDMS, the viscosity is about 80000 cSt (25° C.) | Momentive Performance Materials Japan (Chiyoda-ku, Tokyo, Japan) |
| YF3807 | Silanol end group-containing linear PDMS, the viscosity is about 20000 cSt (25° C.) | Momentive Performance Materials Japan (Chiyoda-ku, Tokyo, Japan) |
| YF3057 | Silanol end group-containing linear PDMS, the viscosity is about 3000 cSt (25° C.) | Materials Japan (Chiyoda-ku, Momentive Performance Tokyo, Japan) |
| TSF451-100 M | −30 FI cs (KF-96 H-Otrimethylsilyl end group-containing linear PDMS, the fluid viscosity is 1,000,000 cSt (25° C.) | Momentive Performance Materials Japan (Chiyoda-ku, Tokyo, Japan) |

[1] the abbreviated name in Table is shown in parentheses

The test methods used in the examples are as follows.

Peel Force

The peel force at 180° was measured by using SUS304, a PVC tube containing a plasticizer (the PVC tube was cut open and applied on a stainless steel panel), and a woven surgical tape (3M DURAPORE surgical tape) (the surgical tape was applied on a stainless steel panel so that the tape to be used for the evaluation was applied on the woven fabric surface of the surgical tape) as the substrate.

A tape was applied on each substrate, and pressure bonded by rolling a roller having a weight of 2 kg back and forth. The tape was immediately peeled from the substrate at an angle of 180° at a peel speed of 300 mm/min. For SUS304, the failure mode was also observed.

The self-adhesive force (T type peel force) was measured. Each tape was folded, adhering the pressure-sensitive adhesive surfaces to each other, and pressure bonded by rolling a roller having a weight of 2 kg back and forth. The tape was immediately peeled from the self-adhering surface in T type peel mode at a peel speed of 300 mm/min.

For all examples and comparative examples, the criteria of the overall evaluation in peel force was as follows. Tape samples in which the peel force and the self-adhesive force to three types of substrates were all 6 N/25 mm or greater was considered as "excellent". Tape samples in which at least one of the peel force and the self-adhesive force to three types of substrates was less than 4 N/25 mm was considered as "poor". Tape samples other than those considered as excellent and poor were considered as "good".

Skin Panel Test

Skin panel tests were carried out by the following procedures. A tape was cut into a tape sample having a size of 25 mm×75 mm. Each tape sample was applied on the inner side of the forearm of five subjects (Panels A to E). Each tape sample was kept on the skin for 1 day, and then the subject removed the tape sample from his/her forearm carefully. The removed tape sample was stained red with azorubine (azo dye) which stains keratin.

(1) Pain Score

The pain when the subject removes the tape from the skin was scored. The score was on a scale from 0 to 10 points (by 1 point increments). The score "0" meant no pain, and the score "10" was severe pain. The average of the scores for Panels A to E was recorded as the pain score.

(2) Keratin Removal Score

The amount of the removed keratin was scored by the brightness of the stained tape surface. The determination of the keratin removal score was carried out as follows. The stained tape surface was scanned in full-color mode. The slice of 5 to 10 mm from the edge of the scanned data was cut and excluded from the sample for changing the gray scale. The full-color image (RGB image) was changed to 256 grades gray scale following the equation: gray=R (red)×0.3+G (green)×0.59+B (blue)×0.11. Among the changed 256 grades gray scale, "255" is the brightest score and "0" is the darkest score. The average absolute brightness of the resulting gray scale image was calculated. The absolute brightness score was calculated by subtracting the resulting average absolute brightness from 255. The relative brightness score was obtained by subtracting the absolute brightness score of the control from the absolute brightness score of each panel. The absolute brightness score of the control was obtained by staining the tape without applying to skin and changing gray scale in the similar procedure. The average of the relative brightness score for Panels A to E was recorded as the keratin removal score.

Since the absolute brightness score is a value obtained by subtracting the average absolute brightness from 255, higher absolute brightness score means that the average brightness score of the stained tape is smaller, that is, the gray scale score is darker. On the other hand, since the relative brightness score is a value obtained by subtracting the absolute brightness score of the control from the absolute brightness score of the tape applied to skin, smaller relative brightness score means that the keratin removal is decreased, which is preferred.

Preparation of Silicone Pressure-Sensitive Adhesive Composition A

Twenty parts by weight of Elastomer 350N, 40 parts by weight of MQ 803 TF, 25.71 parts by weight of heptane, and 0.43 parts by weight of 28% aqueous ammonia solution were mixed (the solid content is 70 weight %). The mixture was heated at 40° C. and kept at that temperature for 24 hours to carry out the condensation reaction of the silanol end group-containing linear PDMS and MQ resin. The reaction product was cooled to room temperature, 40 parts by weight of KF-96H-1-1,000,000 cs and 17.14 parts by weight of heptane were added to the mixture to prepare the silicone pressure-sensitive adhesive composition A (the solid content was 70 weight %).

Preparation of Silicone Pressure-Sensitive Adhesive Composition B

The silicone pressure-sensitive adhesive composition B (the solid content was 70 weight %) was prepared in a similar procedure as for the silicone pressure-sensitive adhesive composition A as, except that the formulation was changed as described in Table 2.

Preparation of Silicone Pressure-Sensitive Adhesive Composition C

Sixty parts by weight of Elastomer 350 N, 40 parts by weight of MQ 803 TF, 77.57 parts by weight of heptane, and 0.50 parts by weight of 28% aqueous ammonia solution were mixed (the solid content was 56 weight %). The mixture was heated at 40° C. and kept at that temperature for 24 hours to carry out the condensation reaction of the silanol end group-containing linear PDMS and MQ resin. The reaction product was cooled to room temperature to prepare the silicone pressure-sensitive adhesive composition C (the solid content is 56 weight %).

Preparation of Silicone Pressure-Sensitive Adhesive Composition D

The silicone pressure-sensitive adhesive composition D (the solid content is 70 weight %) was prepared by mixing 60 weight % of AK 1,000,000, 40 weight % of MQ 803 TF, and 42.86 weight % of toluene.

Example 1

The silicone pressure-sensitive adhesive composition A was applied on the substrate which was obtained by heat laminating a polyester elastomer film having a thickness of 25 μm to a non-woven fabric with a knife coater so that the dried film thickness was 100 μm. The applied film was cured with an electron beam having a dose of 2.6 Mrad and an accelerating voltage of 210 keV. The surface of the pressure-sensitive adhesive was coated with a PET liner having a fluorinated coating to produce a pressure-sensitive adhesive tape.

Example 2

The silicone pressure-sensitive adhesive composition B was applied on the substrate of Example 1 with a knife coater so that the dried film thickness was 100 μm. The applied film was cured with an electron beam having a dose of 3.2 Mrad and an accelerating voltage of 210 keV. The surface of the pressure-sensitive adhesive was coated with a PET liner having a fluorinated coating to produce a pressure-sensitive adhesive tape.

Comparative Example 1

The silicone pressure-sensitive adhesive composition C was applied on the substrate of Example 1 with a knife coater so that the dried film thickness was 100 μm. The applied film was cured with an electron beam having a dose of 0.7 Mrad and an accelerating voltage of 210 keV. The surface of the pressure-sensitive adhesive was coated with a PET liner having a fluorinated coating to produce a pressure-sensitive adhesive tape.

Comparative Example 2

The silicone pressure-sensitive adhesive composition D was applied on the substrate of Example 1 with a knife coater so that the dried film thickness was 100 μm. The applied film was cured with an electron beam having a dose of 3.9 Mrad and an accelerating voltage of 210 keV. The surface of the pressure-sensitive adhesive was coated with a PET liner having a fluorinated coating to produce a pressure-sensitive adhesive tape.

The formulations and EB doses in Examples 1 to 2 and Comparative Example 1 and Comparative Example 2 are shown in Table 2, the evaluation results in peel force is shown in Table 3, and the evaluation results in skin panel test is shown in Table 4. The EB doses in each Example was adjusted to the minimum dose in which the result of no residue is obtained in SUS peel mode.

TABLE 2

| (the formulation is based on parts by weight) | | | | | |
|---|---|---|---|---|---|
| Silanol end group-containing linear PDMS | | Trimethylsilyl end group-containing linear PDMS | | MQ resin | EB dose |
| 350 N | YF 3802 | KF-96 H-1 M | AK 1M | MQ 803 TF | (Mrad) |
| Example 1 | 20 | — | 40 | — | 40 | 2.6 |
| Example 2 | — | 20 | 40 | — | 40 | 3.2 |
| Comparative Example 1 | 60 | — | — | — | 40 | 0.7 |
| Comparative Example 2 | — | — | — | 60 | 40 | 3.9 |

TABLE 3

| | Peel force (N/25 mm) | | | | Overall evaluation of peel force | SUS peel mode |
|---|---|---|---|---|---|---|
| | SUS | PVC | Durapore (trade name) | self-adhesive | | |
| Example 1 | 4.57 | 4.35 | 4.41 | 5.52 | Good | No residue |
| Example 2 | 4.02 | 4.22 | 4.69 | 4.87 | Good | No residue |
| Comparative Example 1 | 5.97 | 5.77 | 6.72 | 8.01 | Good | No residue |
| Comparative Example 2 | 4.28 | 3.84 | 4.64 | 4.84 | Good | No residue |

TABLE 4

| | Pain score (average) | Keratin removal score (average) | Overall evaluation of skin panel test |
|---|---|---|---|
| Example 1 | 1.2 | 27.6 | Excellent |
| Example 2 | 1.0 | 37.4 | Excellent |
| Comparative Example 1 | 2.0 | 57.7 | Poor |
| Comparative Example 2 | 1.6 | 26.1 | Good |

The criteria of the overall evaluation in the skin panel test was as follows. For pain score, the rating score of 1.5 or less is considered as excellent, greater than 1.5 and 1.8 or less is considered as good, and greater than 1.8 is considered as poor. For keratin removal score, 40 or less is considered as excellent, greater than 40 and 50 or less is considered as good, and greater than 50 is considered as poor. When both pain score and keratin removal score are excellent, the overall evaluation is considered as excellent. When at least one of pain score and keratin removal score is poor, the overall evaluation is considered as poor, and the other score is considered as good. Pain score, keratin removal score and overall evaluation cannot be compared directly when the condition of interest (for example, the required adhesive force) is different.

Preparation of Silicone Pressure-Sensitive Adhesive Composition E

A mixture of 20 parts by weight of Elastomer 350N, 40 parts by weight of TSF451-100M, and 40 parts by weight of MQ 803 TF was heated at 85° C. and dissolved by stirring the mixture in a planetary mixer for 1 hour. Next, 0.5 parts by weight of 28% aqueous ammonia solution was added to the mixture and stirred at 85° C. for 1 hour in a closed system. Again, 0.25 parts by weight of 28% aqueous ammonia solution was added to the mixture and stirred at 85° C. for 1.5 hours. The aqueous ammonia solution was stripped at 85° C. under reduced pressure for 1 hour to prepare the silicone pressure-sensitive adhesive composition E.

Preparation of Silicone Pressure-Sensitive Adhesives F to K and M

The silicone pressure-sensitive adhesive compositions F to K and M were prepared in the similar procedure as for the silicone pressure-sensitive adhesive composition as pressure-sensitive adhesive composition E, except that the formulation was changed as described in Table 5.

Preparation of Silicone Pressure-Sensitive Adhesive Composition L

The silicone pressure-sensitive adhesive composition L was prepared by heating a mixture of 60 parts by weight of AK1,000,000 and 40 parts by weight of MQ 803 TF at 85° C. and stirring in a planetary mixer for 1 hour.

Example 3

The silicone pressure-sensitive adhesive composition E was heated to 140° C., and hot melt applied on the substrate of Example 1 with a knife coater so that the dried film thickness was 100 μm. The applied film was cured with an electron beam having a dose of 2.5 Mrad and an accelerating voltage of 210 keV. The surface of the pressure-sensitive adhesive was coated with a PET liner having a fluorinated coating to produce a pressure-sensitive adhesive tape.

Examples 4 to 9 and Comparative Example 3 and Comparative Example 4

Silicone pressure-sensitive adhesive tapes were produced by the procedure described in Example 3 with the silicone pressure-sensitive adhesive composition and EB dose described in Table 5.

Reference Example 1

The surgical tape 3M TRANSPORE containing an acrylic-based adhesive was used.

Reference Example 2

The adhesive bandage NICHIBAN containing a rubber-based adhesive was used.

The formulations and EB doses in Examples 3 to 9 and Comparative Example 3 and Comparative Example 4 are shown in Table 5. The EB doses in each example was adjusted to the minimum dose in which the result of no residue is obtained in SUS peel mode. The evaluation results of the peel forces in Examples 3 to 9 and Comparative Example 3 and Comparative Example 4 are shown in Table 6. The evaluation results of the skin panel tests for Examples 3 to 5, Examples 7 to 9, Comparative Example 4, and Reference example 1 and Reference example 2 are shown in Table 7.

TABLE 5

(the formulation is based on parts by weight)

| | Pressure-sensitive adhesive composition | Silanol end group-containing linear PDMS | | | | Trimethylsilyl end group-containing linear PDMS | | | | MQ resin MQ803TF | EB dose (Mrad) |
|---|---|---|---|---|---|---|---|---|---|---|---|
| | | 350 N | YF 3802 | YF 3807 | YF 3057 | TSF451-100 M | AK 1 M | KF-96 H-0.3 M | AK 60 K | | |
| Example 3 | E | 20 | — | — | — | 40 | — | — | — | 40 | 2.5 |
| Example 4 | F | — | 20 | — | — | 40 | — | — | — | 40 | 3.0 |
| Example 5 | G | — | — | 20 | — | 40 | — | — | — | 40 | 3.3 |
| Example 6 | H | — | — | — | 20 | 40 | — | — | — | 40 | 3.9 |
| Example 7 | I | — | — | — | — | — | — | 40 | — | 40 | 3.2 |
| Comparative Example 3 | L | — | — | — | — | — | 60 | — | — | 40 | 5.1 |
| Comparative Example 4 | M | — | — | — | — | — | — | — | 40 | 40 | 4.1 |
| Example 8 | J | — | — | — | — | 30 | — | — | — | 50 | 3.8 |
| Example 9 | K | — | — | — | — | 40 | — | — | — | 50 | 4.8 |

TABLE 6

|  | Pressure-sensitive adhesive composition | Peel force (N/25 mm) | | | Self-adhesive | Overall evaluation of peel force | SUS peel mode |
| --- | --- | --- | --- | --- | --- | --- | --- |
|  |  | SUS | PVC | Durapore (trade name) |  |  |  |
| Example 3 | E | 5.19 | 4.48 | 6.69 | 6.94 | Good | No residue |
| Example 4 | F | 5.27 | 4.63 | 6.65 | 6.3 | Good | No residue |
| Example 5 | G | 4.79 | 4.45 | 5.44 | 7.2 | Good | No residue |
| Example 6 | H | 4.55 | 4.75 | 5.21 | 5.55 | Good | No residue |
| Example 7 | I | 5.15 | 4.68 | 6.80 | 6.96 | Good | No residue |
| Comparative Example 3 | L | 4.28 | 3.84 | 4.64 | 4.84 | Poor | No residue |
| Comparative Example 4 | M | 3.82 | 3.36 | 5.62 | 4.88 | Poor | No residue |
| Example 8 | J | 8.09 | 6.14 | 8.64 | 10.51 | Excellent | No residue |
| Example 9 | K | 7.48 | 6.38 | 8.43 | 6.56 | Excellent | No residue |
| Comparative Example 1 | — | 8.76 | 10.01 | 1.03 | 9.66 | Poor | No residue |
| Comparative Example 2 | — | 3.16 | 3.03 | 2.01 | 7.67 | Poor | No residue |

TABLE 7

|  | Pain score (average) | Keratin removal score (average) | Overall evaluation of skin panel test |
| --- | --- | --- | --- |
| Example 3 | 2.6 | 52.0 | Excellent |
| Example 4 | 2.6 | 44.2 | Excellent |
| Example 5 | 2.4 | 53.6 | Excellent |
| Example 7 | 1.4 | 53.8 | Excellent |
| Comparative Example 4 | 1.6 | 55.5 | Excellent |
| Example 8 | 3.6 | 67.3 | Good |
| Example 9 | 3.0 | 68.7 | Good |
| Reference example 1 | 4.0 | 103.5 | Poor |
| Reference example 2 | 4.0 | 104.6 | Poor |

The criteria of the overall evaluation in skin panel test in Table 7 were as follows. For pain score, the rating score of 3.0 or less is considered as excellent, greater than 3.0 and 4.0 or less is considered as good, and greater than 4.0 is considered as poor. For keratin removal score, 60 or less is considered as excellent, greater than 60 and 70 or less is considered as good, and greater than 70 is considered as poor. When both pain score and keratin removal score are excellent, the overall evaluation is considered as excellent. When at least one of pain score and keratin removal score is poor, the overall evaluation is considered as poor, and the other score is considered as good. Pain score, keratin removal score and overall evaluation cannot be compared directly when the condition of interest (for example, the required adhesive force) is different.

Example 10

The silicone pressure-sensitive adhesive composition N having a solid content of 70 weight % was prepared by mixing 50 weight % (solid content) of KR-100, 40 weight % of AK1,000,000 and 10 weight % of MQ 803 TF. The silicone pressure-sensitive adhesive composition N contained 39 parts by weight of MQ resin in total. The silicone pressure-sensitive adhesive composition N was applied on the substrate of Example 1 with a knife coater so that the dried film thickness was 100 μm. The applied film was cured with an electron beam having a dose of 1.2 Mrad and an accelerating voltage of 210 keV. The EB dose in this Example was adjusted to the minimum dose in which the result of no residue is obtained in SUS peel mode. The surface of the pressure-sensitive adhesive was coated with a PET liner having a fluorinated coating to produce a pressure-sensitive adhesive tape. The evaluation results of the peel forces in Example 10 are shown in Table 8.

TABLE 8

|  | Pressure-sensitive adhesive composition | Peel force (N/25 mm) | | | self-adhesive peel force | Overall evaluation of peel force | SUS peel mode |
| --- | --- | --- | --- | --- | --- | --- | --- |
|  |  | SUS | PVC | Durapore (trade name) |  |  |  |
| Example 10 | N | 5.22 | 5.00 | 6.79 | 6.89 | Good | No residue |

It is clear to those skilled in the art that various modifications and changes can be made without deviating from the scope and spirit of the present disclosure.

What is claimed is:

1. A silicone pressure-sensitive adhesive, comprising a reaction product of a composition comprising:
    a silanol end group-containing linear organopolysiloxane;
    a non-functional linear organopolysiloxane; and
    a silicate resin,
   wherein the molar equivalent of silanol groups in the silicate resin is greater than the molar equivalent of silanol groups in the silanol end group-containing linear organopolysiloxane, such that unreacted silicate resin remains after a condensation reaction between the silanol end group-containing linear organopolysiloxane and the silicate resin, and
   wherein the dynamic viscosity of the non-functional linear organopolysiloxane at 25° C. is 100,000 mm$^2$/sec or greater.

2. A silicone pressure-sensitive adhesive, comprising a cured product of a composition comprising:
    an end-capped linear organopolysiloxane with a silicate resin, which is a condensation product of a silanol end group-containing linear organopolysiloxane and a silicate resin;
    a non-functional linear organopolysiloxane; and
    a silicate resin, wherein the silicate resin is contained in an amount from 30 to 70 parts by weight in the silicone pressure-sensitive adhesive based on 100 parts by weight of the solid content of the silicone pressure-sensitive adhesive, wherein the dynamic viscosity of the non-functional linear organopolysiloxane at 25° C. is 100,000 mm²/sec or greater.

3. The silicone pressure-sensitive adhesive according to claim 2, wherein the silanol end group-containing linear organopolysiloxane is represented by Formula (1):

Formula 1

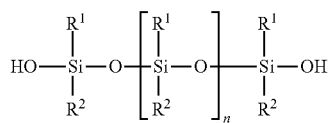
(1)

where in Formula (1), each $R^1$ and $R^2$ is independently an aliphatic hydrocarbon group having 1 to 6 carbon atoms or a phenyl group; a plurality of $R^1$s are identical or different from each other; a plurality of R e s are identical or different from each other; and n is an integer of 1 or greater.

4. The silicone pressure-sensitive adhesive according to claim 2, wherein the non-functional linear organopolysiloxane is represented by Formula (2):

Formula 2

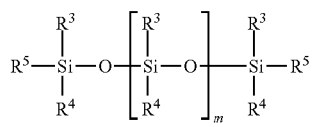
(2)

where in Formula (2), each $R^3$, $R^4$ and $R^5$ is independently an alkyl group having 1 to 6 carbon atoms or a phenyl group; a plurality of $R^3$s are identical or different from each other; a plurality of $R^4$s are identical or different from each other; a plurality of $R^5$s are identical or different from each other; and n is an integer of 1 or greater.

5. The silicone pressure-sensitive adhesive according to claim 2, wherein the silanol end group-containing linear organopolysiloxane is a silanol end group-containing linear polydimethylsiloxane.

6. The silicone pressure-sensitive adhesive according to claim 2, wherein the non-functional linear organopolysiloxane is a trimethylsilyl end group-containing linear polydimethylsiloxane.

7. The silicone pressure-sensitive adhesive according to claim 2, wherein the silicate resin is an MQ resin.

8. The silicone pressure-sensitive adhesive according to claim 2, wherein the non-functional linear organopolysiloxane is cross-linked via its organic side chain group.

9. The silicone pressure-sensitive adhesive according to claim 2, wherein the silicone pressure-sensitive adhesive is essentially free of a residue of a catalyst and a reaction initiator.

10. The silicone pressure-sensitive adhesive according to claim 2, wherein the silicone pressure-sensitive adhesive is a medical sensitive adhesive which is gentle for skin.

11. A silicone pressure-sensitive adhesive composition, comprising:
a silanol end group-containing linear organopolysiloxane;
a non-functional linear organopolysiloxane; and
a silicate resin, wherein the molar equivalent of silanol groups in the silicate resin is greater than the molar equivalent of silanol groups in the silanol end group-containing linear organopolysiloxane, such that unreacted silicate resin remains after a condensation reaction between the silanol end group-containing linear organopolysiloxane and the silicate resin, and wherein the dynamic viscosity of the non-functional linear organopolysiloxane at 25° C. is 100,000 mm²/sec or greater.

12. The silicone pressure-sensitive adhesive composition according to claim 11, wherein the silicate resin is contained in an amount from 30 to 70 parts by weight in the silicone pressure-sensitive adhesive composition based on 100 parts by weight of the solid content of the silicone pressure-sensitive adhesive composition.

13. The silicone pressure-sensitive adhesive composition according to claim 11, wherein the molar equivalent of a silanol group in the silicate resin is greater than that of a silanol group in the silanol end group-containing linear organopolysiloxane.

14. The silicone pressure-sensitive adhesive composition according to claim 11, wherein the non-functional linear organopolysiloxane is contained in an amount from 30 to 60 parts by weight in the silicone pressure-sensitive adhesive composition based on 100 parts by weight of the solid content of the silicone pressure-sensitive adhesive composition.

15. The silicone pressure-sensitive adhesive composition according to claim 11, comprising a linear organopolysiloxane, the end of which being capped with a silicate resin which is a condensation product of the silanol end group-containing linear organopolysiloxane and the silicate resin.

16. The silicone pressure-sensitive adhesive composition according to claim 11, wherein the silicone pressure-sensitive adhesive composition is essentially free of a catalyst and a reaction initiator.

17. The silicone pressure-sensitive adhesive composition according to claim 11, further comprising an organohydrogen polysiloxane and a hydrosilylation catalyst, wherein at least one of the silanol end group-containing linear organopolysiloxane and the silicate resin has an alkenyl group.

* * * * *